United States Patent [19]

Vieth

[11] Patent Number: 5,532,229
[45] Date of Patent: Jul. 2, 1996

[54] TOPICAL ADMINISTRATION OF VITAMIN D TO MAMMALS

[76] Inventor: Reinhold W. Vieth, 27 Chester Hill Road, Toronto, Ontario, Canada, M4K 1X4

[21] Appl. No.: 237,170

[22] Filed: May 3, 1994

[51] Int. Cl.⁶ ................................................. A61K 31/595
[52] U.S. Cl. ............................................ 514/168; 514/947
[58] Field of Search ...................................... 514/168, 947

[56] References Cited

U.S. PATENT DOCUMENTS

| | | | |
|---|---|---|---|
| 2,060,228 | 11/1991 | Lorenz | 167/58 |
| 3,981,996 | 9/1976 | Leigh | 424/243 |
| 4,310,511 | 1/1982 | Holick | 424/59 |
| 4,335,120 | 6/1982 | Holick et al. | 424/236 |
| 5,380,528 | 1/1995 | Alban et al. | 424/401 |

OTHER PUBLICATIONS

Skin Care Products: A and D Ointments (1992).
Holick, et al: "The Production of 1α,25–Dihydroxyvitamin D, in Skin"; The New England Journal of Medicine, vol. 303, No. 7, Aug. 14, 1980, pp. 349–354.

Haddad et al: "Human Plasma Transport of Vitamin D after its Endogenous Synthesis", The American Society for Chemical Investigation, Inc., vol. 91, Jun. 1993, pp. 2552–2555.

*Primary Examiner*—Kimberly Jordan
*Attorney, Agent, or Firm*—Cushman Darby & Cushman

[57] ABSTRACT

A method of delivering a nutritional or therapeutic amount of vitamin D to the blood of a mammal, which method comprises topically administering to the skin of the mammal a vitamin D nutritionally or therapeutically-effective amount of a composition comprising a nutritional or therapeutically effective amount of vitamin D in a suitable pharmaceutically-acceptable carrier, diluent or adjuvant therefor and compositions therefor. The method provides a more suitable, safer and efficient way of providing a mammal with its daily vitamin D intake.

7 Claims, 7 Drawing Sheets

TOPICAL ADMINISTRATION OF VITAMIN D TO MAMMALS

FIELD OF THE INVENTION

This invention relates to Vitamin D nutrition and particularly to Vitamin D compositions and topical administration thereof to mammalian skin.

BACKGROUND TO THE INVENTION

A balanced level of vitamin D has long been recognized as essential to health. Vitamin D appears to increase the efficiency of the intestines to absorb calcium and also mobilizes calcium from bone tissue when required. A deficiency in vitamin D leads to rickets, a debilitating bone disease while excessive levels of vitamin D are toxic. Although use of vitamin D as a food supplement has significantly reduced the incidence of disease caused by vitamin D deficiency, vitamin D is not a naturally occurring nutrient and is present only in low levels in few foods. Oral delivery of vitamin D has been described as ineffective, unnatural and potentially dangerous since toxic amounts of vitamin D may be inadvertently ingested. All recorded cases of vitamin D toxicity have resulted from oral delivery of toxic amounts.

The skin is a major site of cholesterol production and humans naturally acquire vitamin D through the action of ultraviolet light on the skin. 7-Dehydrocholesterol, which is unstable to ultraviolet light, is along the metabolic pathway toward cholesterol. Ultraviolet light breaks open the B-ring of the 7-dehydrocholesterol molecule to generate previtamin $D_3$, which spontaneously isomerizes over hours and days into vitamin $D_3$. An unknown proportion of the vitamin $D_3$ from the skin is absorbed into the circulation. Unabsorbed previtamin $D_3$ and vitamin $D_3$ are made non-functional in the skin by oxidation or by the action of ultraviolet light. Vitamin $D_3$ is not soluble in water, and in the circulation, there is a protein that specifically binds to and carries vitamin D and its metabolites. The advantage of ultraviolet exposure is that it has no vitamin D toxicity associated with it. The disadvantage is that the availability of ultraviolet light is unreliable, too much of it causes cancer, and at northern latitudes there is not always enough ultraviolet light intensity outdoors to generate previtamin $D_3$.

To become effective, vitamin D must go through two metabolic steps. Vitamin D is readily changed by the liver to 25-hydroxyvitamin D, which is measured in serum to reflect vitamin D nutritional status. 25-hydroxyvitamin D has little, if any, per se biological activity. The kidney metabolizes 25-hydroxyvitamin D into the active hormone, 1, 25-dihydroxyvitamin D, which affects calcium transport across cell membranes. Production of 1, 25-dihydroxyvitamin D is carefully regulated by the body, according to its mineral requirements.

Very few foods naturally contain vitamin D. Mellanby, *J Physiol* (London) volume 52:1iii (1919), instituted the idea that an artificial supplement, cod-liver oil, contained an agent that prevented rickets; the agent became known as vitamin D. Most of the vitamin D in our food is supplementary, synthetic material, which is either in the form of vitamin $D_3$, the form naturally produced in animals, or it can be vitamin $D_2$, which is derived from a plant steroid. The term, vitamin D, refers to either the $D_2$ or $D_3$ forms. The advantages of adding vitamin D to the diet are well known. The disadvantages are that orally acquired vitamin D can be toxic (reference, Vieth, *Bone and Mineral*, volume 11: 267–272; 1990) and that people with impaired fat absorption will not absorb it well from the gut. Furthermore, it is known that vitamin D behaves differently in the circulation depending on whether it enters via the gut or the skin. Haddad JG, et al *J Clin Invest* volume 91:2552; 1993 showed that oral vitamin $D_2$ enters the circulation mixed with dietary fats in chylomicrons and it becomes partially activated into 25-hydroxyvitamin $D_2$ relatively quickly. In contrast, these authors showed that the vitamin $D_3$ generated from exposure of experimental subjects to ultraviolet lamps will circulate unchanged for a prolonged time when combined with its specific transport protein, i.e. vitamin D-binding protein (DBP), and not with chylomicrons. Fraser, in a review of how the body handles vitamin D, *Lancet*, April 30, 1983:969 concluded, "The oral route as a means of supplying vitamin D is ineffective, unnatural, and potentially dangerous. Yet, to achieve adequate exposure to the sun of whole populations such as those in large cities may well prove impractical. Human ingenuity might therefore have to devise another way of providing vitamin D—one which takes into account the natural physiology of its formation and processing in the human body."

U.S. Pat. No. 2,060,228 issued to Lorenz AJ, describes a soap having incorporated therein an antirachitic factor having beneficial dermatological properties.

Vitamin D together with vitamin A have been added to ointments used for minor skin irritations, diaper rash, chafing, skin dryness, etc., and they are particles. One alternative is, typically, sold as "A & D Ointment".

Vitamin D is fat soluble and is generally administered in such ointments in an oil based vehicle such as petroleum gel, in a vehicle such as propylene glycol. The percutaneous delivery of vitamin D using such ointments is unreliable and likely only locally significant for the following reasons. Vitamin D is very sensitive to sunlight since it is decomposed readily by ultraviolet light. Such ointments are indicated for minor local skin ailments and cannot be a reliable source of the body's vitamin D requirement. The oily vehicles render the ointments unsuitable for general application to the body and staining of clothing would result if so used. Indeed the manufacturers of A&D ointments do not claim any benefit from the presence of the vitamins. The amount of vitamin D delivered using such ointments is likely insignificant due to rapid decomposition in sunlight, and restriction to local intermittent use.

In recognition of the risk of vitamin D deficiency thorough use of sunblocking lotions, vitamin D or its precursors have been added to such lotions. In U.S. Pat. No. 3,981,996 issued to Leigh Sep. 21, 1976 a topical skin cream as a drug delivery system was described. The cream comprised a continuous hydrophobic medium in which were disposed inert water soluble particles. One embodiment in Leigh included vitamins A and D absorbed on such particles within a conventional sunscreen preparation Leigh described a sun screening preparation having mixtures of vitamin A and D in an amount from 50,000 to 5,000,000 I.U. per gram but otherwise does not provide details of the benefits of such delivery or reasons for the recommended concentrations. Presumably the primary focus of Leigh is a drug delivery system wherein vitamin D is only one of the example given. In light of current knowledge of vitamin D toxicity, the concentrations specified by Leigh are potentially toxic. Indeed to provide the phenomenally high vitamin concentration described in Leigh, the use of such a particle delivery system is necessary.

Vitamin $D_3$ has been administered to the shaved skin of rats at a dose of 50 µg in 10 µL 95% ethanol (Holick M. F., Uskokovic M., Henley J. W., MacLaughlin F., Holick S. A., Potts J. T. The photoproduction of 1,25-dihydroxyvitamin $D_3$ in skin—an approach to the therapy of vitamin-D-resistant syndromes. N Engl J Med 1980; 303:349–354). The vitamin $D_3$-treated rats served as a negative control group for which no response was detected; in contrast, application of 1,25$(OH)_2D_3$, or 1,25-dihydroxylated-7-dehydrocholesterol increased intestinal calcium transport and serum calcium in their experiment. A subsequent patent by Holick, U.S. Pat. No. 4,310,511 issued Jan. 12, 1982, indicates that dermal uptake is inefficient and that there could be an "uncontrolled increase in absorption of vitamin D, with concomitant loss of concentration control, and the appearance of side effects such as vitamin D toxicity" (column 3, line 18).

In U.S. Pat. No. 4,310,511 a sunscreen composition is described including a precursor to vitamin D. The precursor or previtamin D is absorbed by the skin and cutaneously synthesized into vitamin D by the natural thermal process of the epidermis as described above. Holick recognizes the risk of vitamin D toxicity and addresses the issue by utilizing only non-hydroxylated steroid precursors in the composition. Holick submits that vitamin D toxicity is due to circulating levels of hydroxylated forms of vitamin D (at positions 1; 1,25; 1,24,25; or 1,23,26). By supplying non-hydroxylated steroids only, Holick states that the natural regulatory mechanisms of the body prevent overproduction of vitamin D from its precursors and resultant toxicity. It is now recognized that the hydroxylations producing potent forms of vitamin D are driven by the vitamin D supply through mass action relationships, Vieth, The Mechanisms Of Vitamin D Toxicity, Bone and Mineral, 11 (1990) 267–272).

It is therefore important to determine the total quantity of vitamin D entering the body and not merely the hydroxylated forms as proposed by Holick. Vitamin D intoxication should be characterized by measurement of the total concentration of all vitamin D metabolites and the concentrations of 1,25 $(OH)_2D$ and DBP. This regulation of total vitamin D intake is required since it is now recognized that a probable mechanism for vitamin D toxicity is that high 25 (OH)D concentration will cause both the excessive synthesis of 1,25 $(OH)_2D$ and together with vitamin D and its other metabolites cause displacement of the hormone from DBP thereby increasing the amount of free 1,25$(OH)_2D$ that is accessible to target cells. Regulation of 1,25$(OH)_2D$, and other selected hydroxylated provitamins as proposed by Holick is not sufficient to prevent toxicity in light of current knowledge.

The amount of vitamin D precursor proposed by Holick is so large that if all of it were synthesized into vitamin D by the epidermis, toxicity would result. Holick's method of replenishing the vitamin D supply has not been proven to be reproducible and likely involves a large degree of error. Since vitamin D is supplied indirectly through selected non-hydroxylated precursors, Holick's method of preventing toxicity involves several unknowns such as the rate and efficiency of previtamin D to vitamin D synthesis, and the effect of DBP displacement.

Notwithstanding the above teachings of the prior there remains a need for a suitable and efficacious method of administering nutritional or therapeutic amounts of vitamin D to humans.

SUMMARY OF THE INVENTION

Surprisingly, I have now found a suitable and efficient method of administering a desired amount of vitamin D to a mammal, which method comprises dermal application of vitamin D in a suitable, pharmaceutically-acceptable carrier.

I have found that the difficulties with previous ways of providing vitamin D may be overcome by the process of dermal application. Thus, process of dermal application eliminates the need to risk exposure to ultraviolet light in order to acquire vitamin D thorough its natural, dermal route. Although oral administration of vitamin D can be toxic, there are no known cases of toxicity due to vitamin D from sun exposure and, hence, from acquiring it dermally.

It is thus an object of the present invention to provide a safe, suitable and efficient method of administering vitamin D to a mammal.

It is a further object of the invention to provide a pharmaceutically-acceptable vitamin D composition for use in said method.

Accordingly, in one aspect, the invention provides a method of delivering a nutritional or therapeutic amount of vitamin D to the blood of a mammal, which method comprises topically administering to the skin of the mammal a vitamin D nutritionally or therapeutically-effective amount of a composition comprising a nutritional or therapeutically effective amount of vitamin D in a suitable pharmaceutically-acceptable carrier, diluent or adjuvant therefor.

I have found that at nutritionally relevant dose levels, dermal application of vitamin D can provide vitamin D nutrition with an efficiency that is comparable to that attained by oral administration of the same dose.

Surprisingly and advantageously, I have found that there is no calcium deposition in the kidney or aorta by topical application of vitamin D to the skin at dosages of the order of three times that which caused calcium deposition in these tissues when vitamin D is administered orally.

I have further found that the application to bare skin of a nutritionally effective amount of vitamin D dissolved in a suitable, pharmaceutically acceptable carrier, will produce an increase in 25-hydroxyvitamin D close to the increase attainable with the same dose given directly into the stomach. The use of a volatile, acceptable carrier vehicle such as for example, ethyl alcohol, for the vitamin D, results in efficient uptake into the body and minimizes the possibility of accidentally wiping off the vitamin D.

The vitamin D compositions of use in the invention may further comprise an antioxidant to serve as a preservative for the vitamin D. Examples of such agents are a-tocopherol (vitamin E), vitamin A, carotene, or butyrated hydroxytoluene (BHT).

The vitamin D may be dermally administered in admixture with pharmaceutically-acceptable, diluents adjuvants or carriers, which may be readily selected by the person skilled in the art and which are able to provide efficacious and efficient uptake of the vitamin D. Preferably, any acceptable liquid or lotion that is capable of dissolving the vitamin D or of maintaining it in an emulsion is within the invention. Preferably, the composition comprise a liquid solvent for vitamin D and most preferably a volatile solvent, such as ethyl alcohol.

The amount of vitamin D in the dermal composition may be readily selected to be that which provides suitable uptake by the skin. For example, a daily single dose may contain from 5 to 4000 μg, preferably 20 to 1000 μg of vitamin D per mL. Weaker compositions, if applied more frequently during the day may contain lesser amounts of vitamin D.

In one aspect, the compositions of the present invention may further comprise a perfume. The combination of vitamin D and perfume will facilitate compliance on the part of patients who should be taking vitamin D, for example, in the treatment or prevention of osteoporosis. The perfume will make the act of taking the vitamin D more pleasant, and it makes it easier both to remember to take the dose, and to recall that a dose was actually applied. The presence or absence of a perfume scent respectively reminds the user whether or not the dose of vitamin D has been applied to the skin.

BRIEF DESCRIPTION OF THE DRAWINGS

In order that the invention may be better understood, a preferred embodiment will now be described by way of example only, with reference to the accompanying drawing wherein.

DESCRIPTION OF A PREFERRED EMBODIMENT AND BEST MODE OF PRACTICE

A vitamin $D_3$ composition was prepared at 8 μg per 50 microliters ethyl alcohol (that is 20 nmol per 50 μL, or 308 international units, per 50 μL).

EXPERIMENTAL

Experiment 1.

A comparison of serum radioactivity after one administration of radiolabelled vitamin $D_3$ via the skin or gut, compared to intravascular injection.

Method.

The protocols and procedures used in this work were approved beforehand by an animal-care committee at the University of Toronto. Wistar rats, 250-g weight and fed normal diet, were divided into three groups of six, and each rat was given 400,000 cpm of [4-4C]-vitamin $D_3$ (57 mCi/mmol, Amersham, UK). One group was given the [$^{14}$C]-vitamin $D_3$ by intracardiac injection; one group was given the tracer through an infant-feeding tube, directly into the stomach; and one group received the dose by application in 50 μL ethanol to a 2×2 cm patch of shaved skin on the lower back. Blood was taken by bleeding 0.25 mL from the tail, from three rats at a time, for each time indicated in the graph, except for the final sample at 3 wk, which is from all rats at the time of killing with an anesthetic overdose. The serum was counted in a Beckman LS6800 beta-counter and results are corrected for background, sample volume, and rat weight.

Results.

Figure 1:
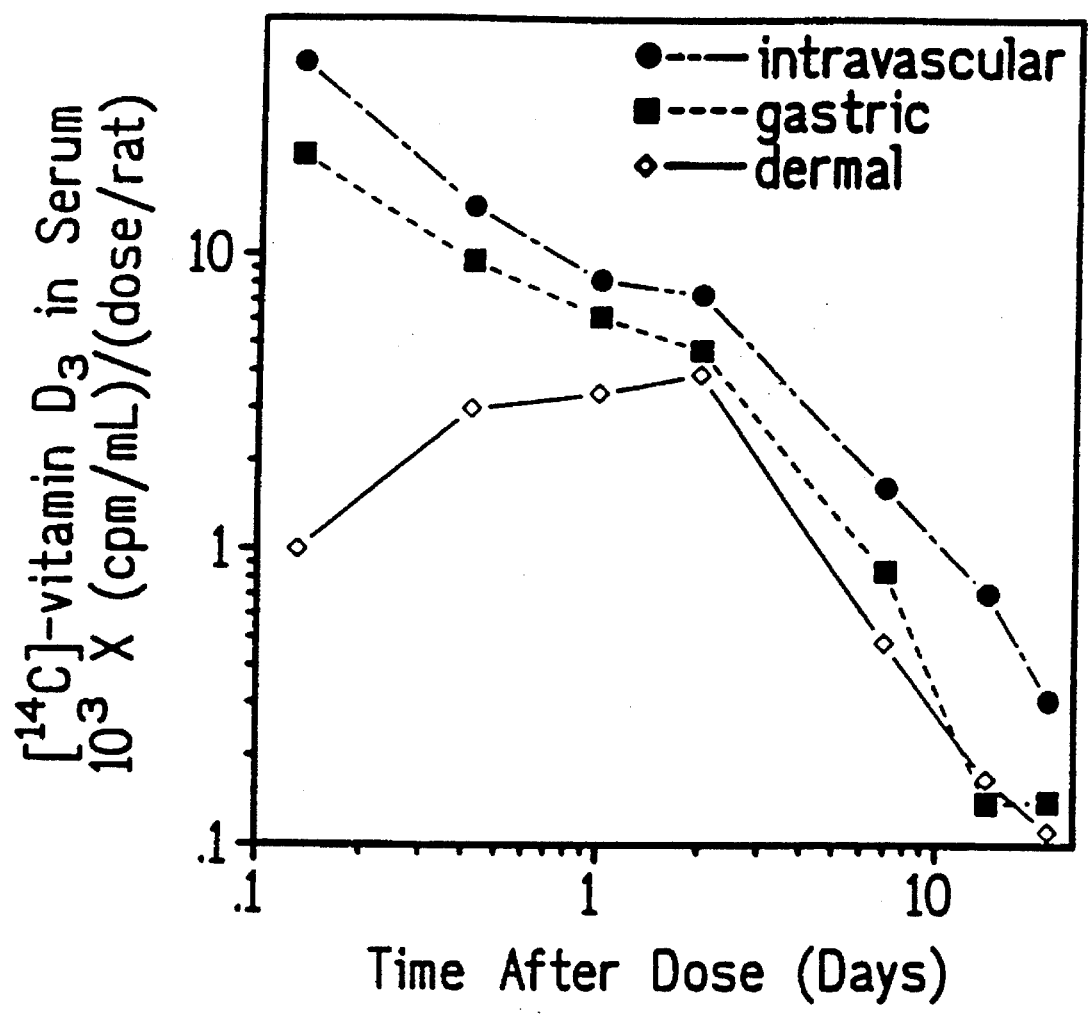
FIG. 1 represents a graph which shows the fraction of the radioactivity given to rats, that was measured in the serum at various times up to 3 weeks after one dose of [$^{14}$C]-vitamin $D_3$ was given either by direct injection into the circulation, by direct instillation into the stomach through a feeding tube, or by application to a shaved area of skin; each dose ($4\times10^5$ cpm) was given by intracardiac injection, or by gastric tube, or by application in ethanol to a shaved area on the back of the rats. Each point is the mean of 3-6 rats.

FIG. 1 shows the mean serum radioactivity at each time point. Vitamin $D_3$ was taken into the circulation by each route. However, based on the final blood samples at 3 wk, both the gastric and dermal groups had less radioactivity in the serum than the intravascular group: in units of fraction of dose, present in 1 mL serum relative to that given per 250-g rat, the vitamin $D_3$ was: skin, 1.11±0.28SD; gastric, 1.40 ±0.41; intravascular, 3.80±2.21, all units are ×10$^{4-}$. All rats in the intravascular group had more tracer in the serum than any of the rats in the other groups, and the mean intravascular radioactivity at 3 wk was significantly higher than either the oral or dermal group (p<0.05 for each, by two-tailed t-test). At 3 wk, the difference in serum radioactivity was not statistically significant between the dermal and oral groups. Also measured for radioactive vitamin $D_3$ were, kidney, liver, and adipose tissues; radioactivity in these tissues was in amounts that paralleled to the serum levels.

The use of radiolabelled material showed that vitamin $D_3$ is taken into the circulation from the skin more slowly than from the gut. In the longer term, the difference in the amount of vitamin $D_3$ in the circulation between oral and dermal administration is negligible. Compared to the direct injection of vitamin $D_3$ into the bloodstream, both dermal and gastric approaches are inefficient, delivering less than half the vitamin $D_3$ into the blood.

Experiment 2.

Uptake of radioactive vitamin $D_3$ from skin or gut during the longer term treatment with vitamin $D_3$ at 20 nmol/day.

The previous experiment 1 involved only one acute dose of a minute, tracer amount of vitamin $D_3$. It remained possible that dermal application could not deliver a larger, more nutritionally relevant amount of vitamin $D_3$. This experiment 2 looked at what happens when vitamin $D_3$ is given during the course of daily treatment with a moderate amount of vitamin $D_3$.

Method.

Male, Wistar rats were obtained at 90–110 g, and placed on 0.5% calcium diet that had a marginal vitamin $D_3$ supply (0.08 µg/15 g). After 30 days, the rats were divided into three groups of 6: one group continued with no supplement, one group was given daily vitamin $D_3$ supplement, 8 µg/day either by gastric tube, the third received the supplement by application to the skin in 50 µL ethanol. Vitamin $D_3$ was given for 3 wk. The day before the rats were killed, the vitamin $D_3$ dose was supplemented with [$^{14}$C]-labelled vitamin $D_3$, 915,000 cpm per rat. Blood was obtained from the tail of each rat at 3 h, 9 h, and by heart puncture when the rats were anesthetized for killing, 24 h after giving the tracer. The blood was extracted and chromatographed to distinguish [$^{14}$C]-vitamin $D_3$ from the [$^{14}$C]-25(OH)$D_3$ generated from it. Radioactivity was also measured in the liver, kidney, and adipose tissue. Serum nonradioactive 25(OH)$D_3$ was also measured.

Results.

Figure 2A:
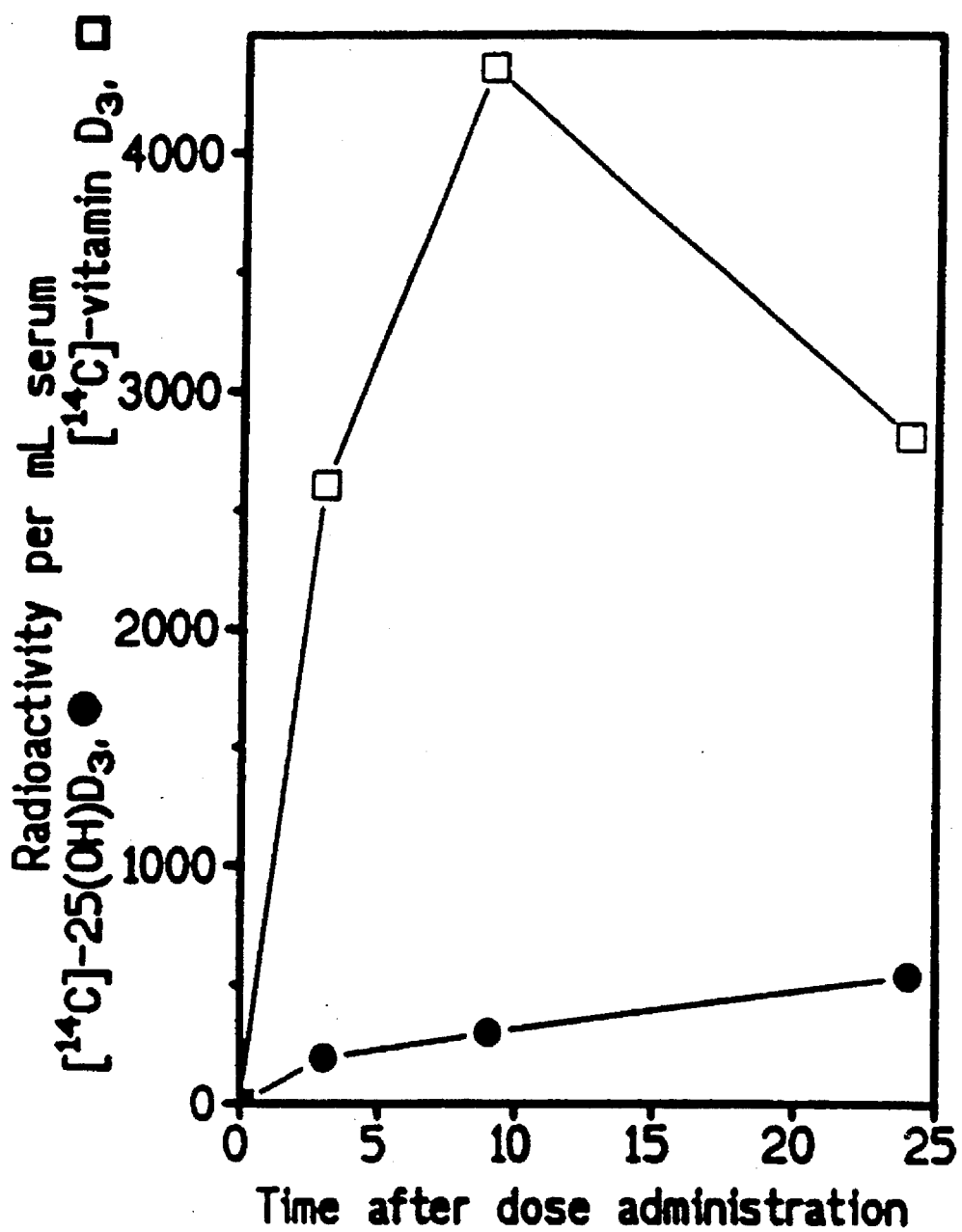
FIG. 2 shows in two graphs the amounts of serum [$^{14}$C]-vitamin $D_3$ and its metabolite, [$^{14}$C]-25(OH)$D_3$ present during the first day after tracer addition to nutritional vitamin $D_3$ supplementation by gastric tube or dermally. One dose of [carbon-14]-labelled vitamin $D_3$ was given at the time of the last of 14 daily doses of nonradioactive vitamin $D_3$. The graphs show the uptake and metabolism of one [$^{14}$C]-vitamin $D_3$ dose during the course of gastric or dermal supplementation with vitamin $D_3$. The tracer was given in addition to the usual, 8 μg/day vitamin $D_3$ dose, and by the same route. Radioactivity in serum was isolated by chromatography to measure that which elutes as vitamin $D_3$, or as 23(OH)$D_3$, Each point is the mean of results from six rats.
Figure 2B:
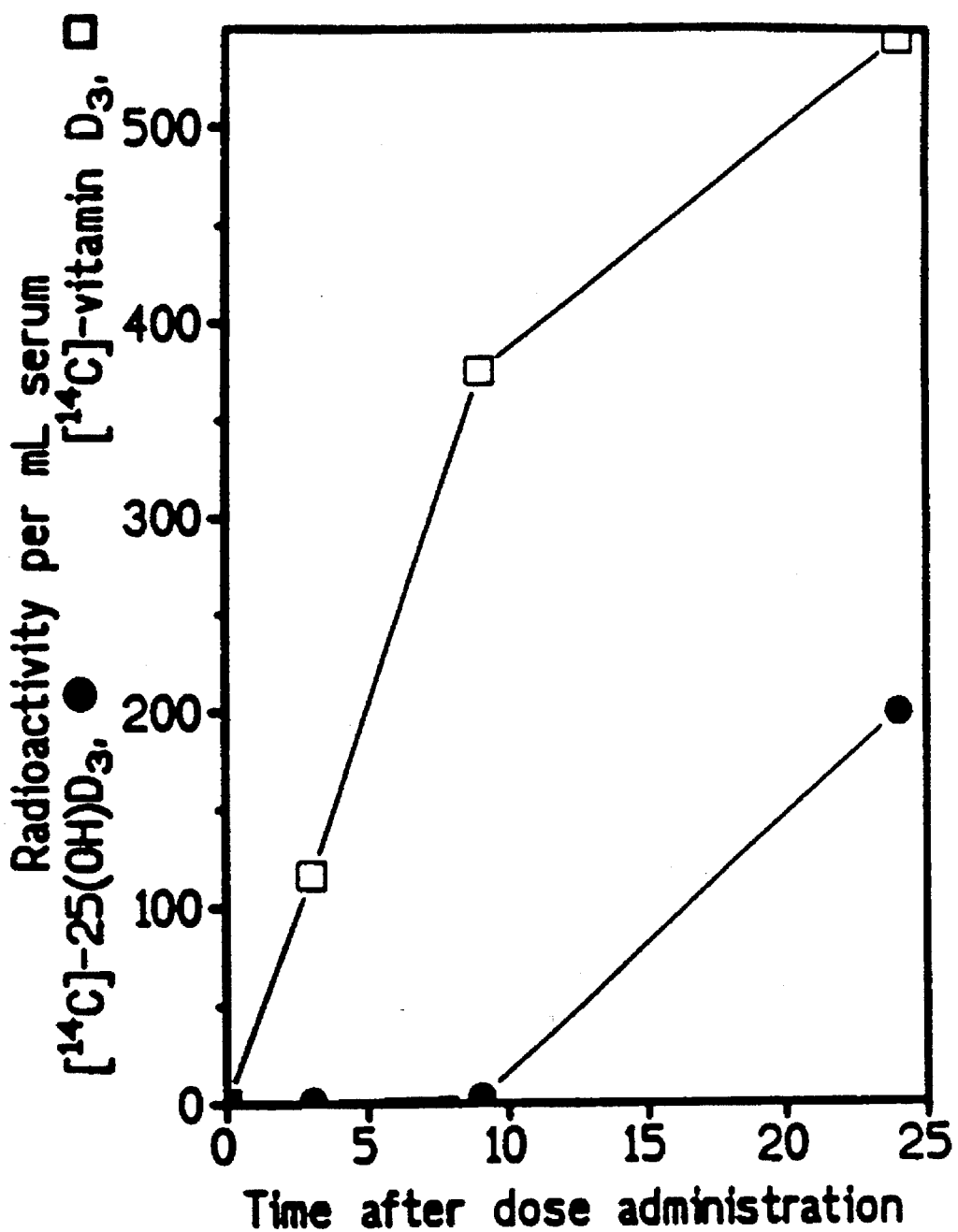

For both gastric and dermal administration, FIG. 2 shows uptake of [$^{14}$C]-vitamin $D_3$ into the serum, and its conversion to [$^{14}$C]-25(OH)$D_3$. With oral dosing, [$^{14}$C]-25(OH)$D_3$ was detected in every sample; however, with dermal administration this metabolite was not evident until 24 h after dosing. By the end of the experiment, rats not given the vitamin $D_3$ supplement had serum 25(OH)$D_3$ levels of 20±9SD nmol/L; those given 8 µg/day by gastric tube had 171±46 nmol/day; those given 8 µg/day onto the skin had 109±14 nmol/day 25(OH)$D_3$. The differences in 25(OH)$D_3$ were all statistically significant among the groups ($p<0.01$, each). Relative to the group receiving only the marginal amount of vitamin $D_3$ in the diet, dermal vitamin $D_3$ raised 25(OH)$D_3$ to 59% of the increase obtained with gastric supplementation.

The addition of radiolabelled vitamin $D_3$ to the last day's dose shows that vitamin $D_3$ is taken into the circulation more slowly when given via the dermal route, compared to the gastric route. The level of vitamin $D_3$ nutrition achieved by the end of 3 weeks of treatment is reflected in the serum 25(OH)$D_3$ concentration. For this, dermal vitamin $D_3$ raised serum 25(OH)$D_3$ to a degree comparable to that achieved with gastric vitamin $D_3$ administration. This shows that dermal administration of vitamin $D_3$ is a viable way to provide vitamin $D_3$ nutrition.

Experiment 3.

Efficacy in the long-term: ability of oral and dermal vitamin $D_3$ delivery to influence serum 1,25(OH)$_2D_3$ levels in response to changes in dietary calcium.

This experiment was conducted to show production of the hormone, 1,25(OH)$_2D_3$, increases to help the body compensate for lower calcium intake. The present experiment[3] was designed to demonstrate that dermally applied vitamin $D_3$ can produce responses to changes in calcium that are comparable to those produced by a gastric vitamin $D_3$ at a similar dose.

Method.

Male, Wistar rats were obtained at 120–130 g, and placed on a 0.01% calcium, 0.7% phosphate diet that was vitamin D deficient (Teklad Test Diets, Madison, WI) this was for one week to help deplete vitamin D stores. For the next three weeks the rats were fed the vitamin D-deficient diet, but with normal, 0.5%, calcium. Starting with these 3 weeks, the rats were divided into four vitamin $D_3$-treatment groups, initially, nine rats per group: group a) supplemented once weekly with 0.6 µg vitamin $D_3$ (average dose, 0.08 µg/day); group b) supplemented once every second day with vitamin $D_3$ to provide 2 nmol/day, i.e., each dose was 4 nmol of vitamin $D_3$; group c) supplemented once every second day with vitamin $D_3$ to provide 8 µg/day. The preceding groups all received the vitamin $D_3$ through an infant-feeding tube inserted through the mouth into the stomach. One group, d), received its vitamin $D_3$ in the ethanol applied onto a shaved 2 cm×2 cm patch of skin on the back, this was done every second day to provide vitamin $D_3$ at 8 µg/day. The volume of each dose of vitamin $D_3$ given was adjusted so that the stated doses are per 250 g body weight. Over a second 3-week period while maintaining the described vitamin $D_3$ dosing regimens, diet calcium content was changed weekly and blood sampling was started (that is, changes in calcium and sampling was from weeks 4 to 6, inclusive, of receiving the appropriate vitamin $D_3$ supplement). Diet calcium was first dropped to 0.01% then raised to 1.5% and finally dropped again to 0.01%. For each week of dietary calcium manipulation, blood was obtained at day zero (the day of but just prior to the change in calcium), and days 1, 3, and 7 after the change. During the first week, 0.5 mL of blood was taken on the first two of these days and anticoagulated with heparin, the cells were isolated and resuspended in normal rat plasma and reinjected into the femoral vein. This procedure resulted in an unacceptable mortality rate over the following day that was probably due to emboli in the reinfused blood. For the subsequent samplings, only 0.2–0.3 mL of blood was taken by bleeding from the tail into precalibrated microcentrifuge tubes. In this way, the bleeds prior to sacrifice removed a net total of less than 2 mL of blood, that is, less than or equal to 10% of the blood volume. Samples of daytime urine was collected into microfuge tubes that were fastened to the cones of metabolic collection funnels designed to hang under the wire cages. The cages and cones were rinsed with 0.1 mol/L hydrochloric acid prior to each collection. To eliminate contamination of the urine with diet, stool or water, the rats were placed into these separate cages only during the urine-collection period, until about 1 mL urine was present in the microfuge tube, this was typically within 5 min to one hour. By the end of the experiment, the rats ranged in weight from 350 to 424 grams, with no weight differences between the groups.

Biochemical measurements. 1,25(OH)$_2D_3$ in serum was measured by calf-thymus receptor-binding assay after initial purification of 1,25(OH)$_2D_3$ with C18-OH cartridges (5). For the serum volumes that were minimal, serum was measured out in 50 µL increments, and the final result was adjusted for the volume of sample analyzed. To measure 1α-hydroxylase in renal mitochondria, the incubation was as described previously, except the substrate was 20 μmol/L nonradioactive 25(OH)D$_3$. The assay was stopped by addition of 2.5 mL methanol. To monitor recovery of 1,25 (OH)$_2$D$_3$, 2000 cpm of [$^3$H]--1,25(OH)$_2$D$_3$ were added in 50 μL ethanol prior to further extraction with two additions of 1.25 mL methylene chloride. The methylene chloride layer was taken and evaporated to dryness, redissolved in hexane, isopropanol, methanol (90:9: 1) for purification by HPLC, Zorbax-Sil column. The material eluting as 1,25(OH)$_2$D$_3$ was evaporated and redissolved in acetonitrile: water for further purification with C18-OH cartridges and quantitation by thymus receptor assay, as described for serum. Renal 24-hydroxylase was measured by incubating mitochondria with [$^3$H]-25(OH)D$_3$ as substrate (Vieth and Fraser, J Biol Chem. 254:12455–12460;1979). Vitamin D-binding capacity was measured, based on the specific uptake of [$^3$H]-25 (OH) D$_3$ by rat serum, involving the removal of non-specifically bound [$^3$H]-25 (OH) D$_3$ with charcoal (Vieth R, Clin Chem 40:435–441; 1994). To measure 25(OH)Ds, 0.2 mL of serum was spiked with 1000 cpm/mL with [$^3$H]-25(OH)D$_3$ (25(OH),26,26[$^3$H]-vitamin D$_3$20 Ci/mmol, Amersham, Oakville, Ont, Canada), extracted and chromatographed. Material eluting at the positions of authentic 25 (OH) D$_3$ was measured with competitive protein-binding assay against standards of crystalline 25(OH)D$_3$ that had been purified by HPLC and quantitated, based on spectral absorbance at 265 nm, assuming 18,300 AU/mol/L. Other biochemical measures were made using routine methods established for the Kodak Ektachem 700, dry-chemistry slide system (Rochester, N.Y.).

Results.

The graphs show the effect of vitamin D$_3$ supplementation on serum 1,25(OH)$_2$D$_3$ hormone levels during periods of different percent diet calcium content (as indicated along the top). Low and normal vitamin D$_3$ intake resulted in similar 1,25(OH)$_2$D$_3$ concentrations. Serum 1,25(OH)$_2$D in the four groups of rats: Note that modestly higher vitamin D intake (oral ●, dermal ♦) resulted in lower 1,25D levels than with low (o) or normal vitamin D (x). Supplementation with 8 μg/day vitamin D$_3$ by either the gastric route (solid circles in top panel), or the dermal route (sold diamonds in lower panel) resulted in similar suppression of 1,25(OH)$_2$D$_3$ at all levels of calcium intake. Table 1 shows more biochemical data for this experiment. The final measurements, made after the 6 weeks of vitamin D$_3$ treatment are presented in TABLE 1. The supply of vitamin D$_3$ influenced serum 25(OH)D$_3$, the measure of vitamin D nutrition, in a manner appropriate for the dose used. All group means for 25(OH)D$_3$ are significantly different from each other. However, the dermal or gastric treatment with 8 μg/day produced similar levels of 25(OH)D$_3$, 127±4 nmol/L, compared to 148±10 nmol/L, respectively. Aside from 25(OH)D$_3$, there were no significant different differences between the dermal or gastric treatment approaches. Other measures of vitamin D efficacy were also affected in the same way by both the dermal and gastric modes of vitamin D$_3$ administration: compared to the groups with less vitamin D$_3$ intake, both 8 μg/day approaches suppressed 1-hydroxylase in kidney, while they increased 24-hydroxylase in kidney.

Figure 3A:
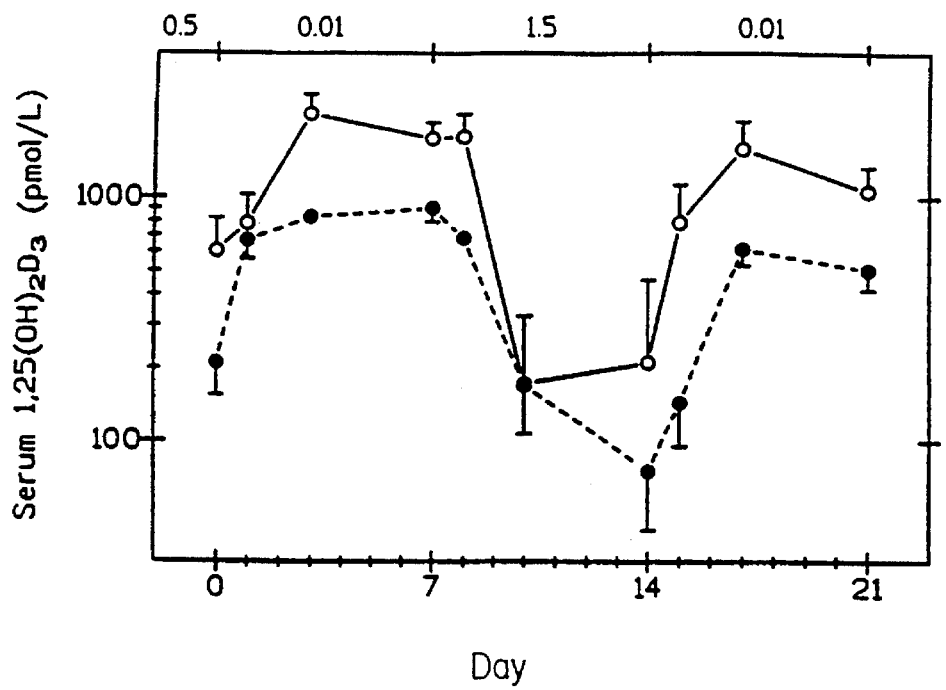
FIG. 3 in two graphs shows that higher vitamin $D_3$ nutrition via either the dermal ♦ or gastric ● route will lower serum 1,25(OH)$_2D_3$ concentrations in rats during weeks of different dietary calcium content.
Figure 3B:
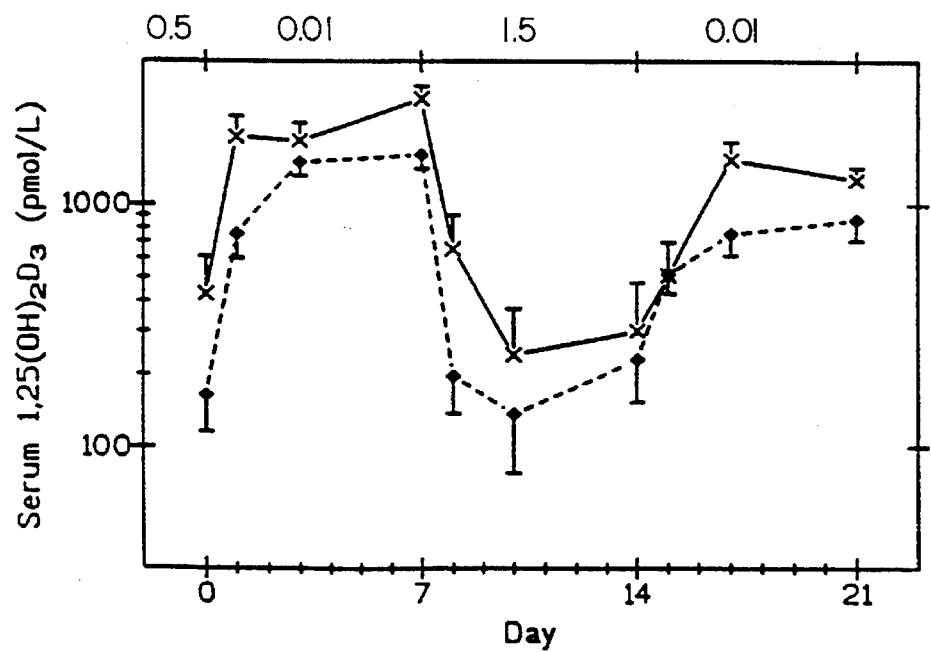

Another effect that was similar, was that 8 μg vitamin D$_3$ per day, either by gastric or dermal route resulted in lower serum 1,25(OH)$_2$D$_3$ at every level of calcium intake than the levels with either 0.08 or 0.8 μg per day (FIG. 3).

It was thus found that with the moderate vitamin D$_3$ supply for rats, of 20 nmol/250 g/day, dermal administration was essentially the same as the oral route, in terms of raising 25(OH)D$_3$ (85% as effective). For other tangible measures of biological response to vitamin D$_3$ intake, namely the activities of renal enzymes that metabolize 25(OH)D$_3$, and the suppression of serum 1,25(OH)$_2$D$_3$ levels, there was no significant difference between the two routes.

Experiment 4.

Toxicity: Short-term responses to increasing doses of vitamin D$_3$ given dermally or by gastric tube.

To compare the efficacy of increasing doses of vitamin D$_3$ in the short term. A fatal oral vitamin D$_3$ dose is 14 days of 2600 μg/day (Sheppard RM and DeLuca HF, Arch Biochem Biophys 1980; 202: 43–55). The present experiment was designed to compare effects of doses up to this level, given by gastric tube or dermally.

Results.

Figure 4:
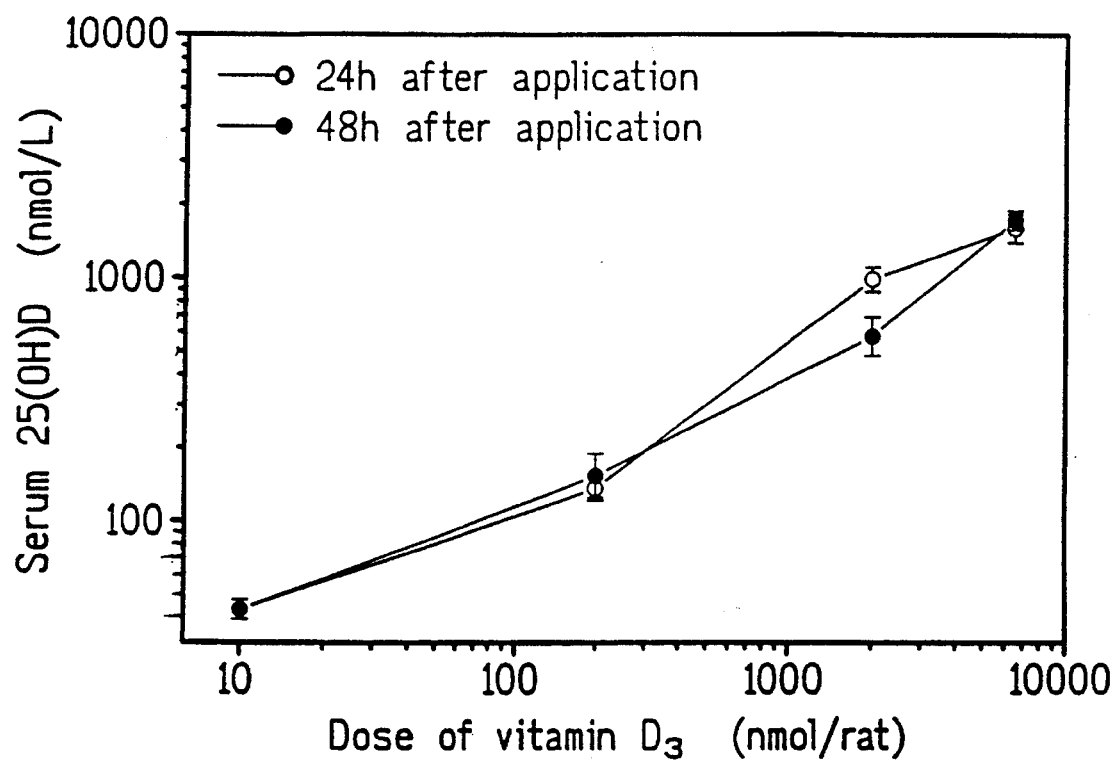
FIG. 4 represents a graph which shows the early serum 25(OH)$D_3$ levels in response to different gastric vitamin $D_3$ doses. During the first 48 hours the serum 25(OH)$D_3$ parallels the vitamin $D_3$ dose, even when the potentially fatal dose of 2600 μg (6500 nmol) is given. Each point represents the mean ±SEM of 7 normal, 250-g rats.
Figure 5:
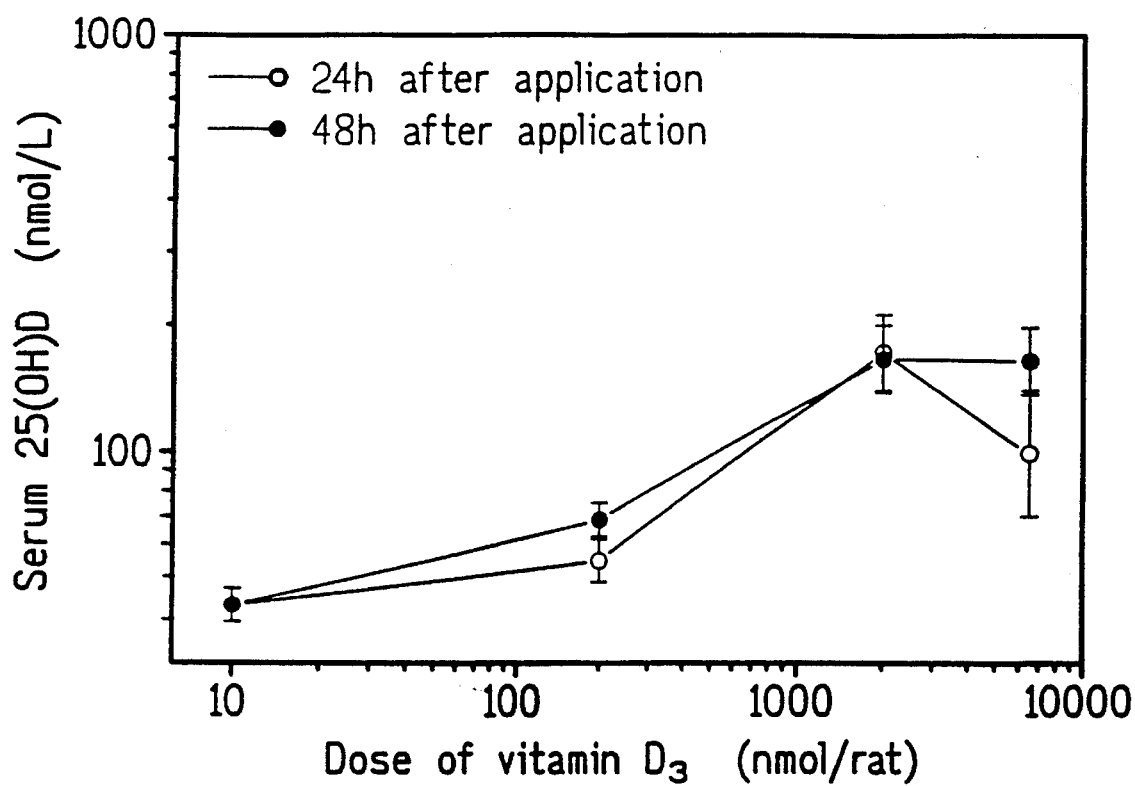
FIG. 5 represents a graph which shows the early serum 25(OH)$D_3$ levels in response to different dermal vitamin $D_3$ doses. During the first 48 hours the serum 25(OH)$D_3$ does not parallel the vitamin $D_3$ dose beyond the 800 μg (2000 nmol)/day dose.
Figure 6:
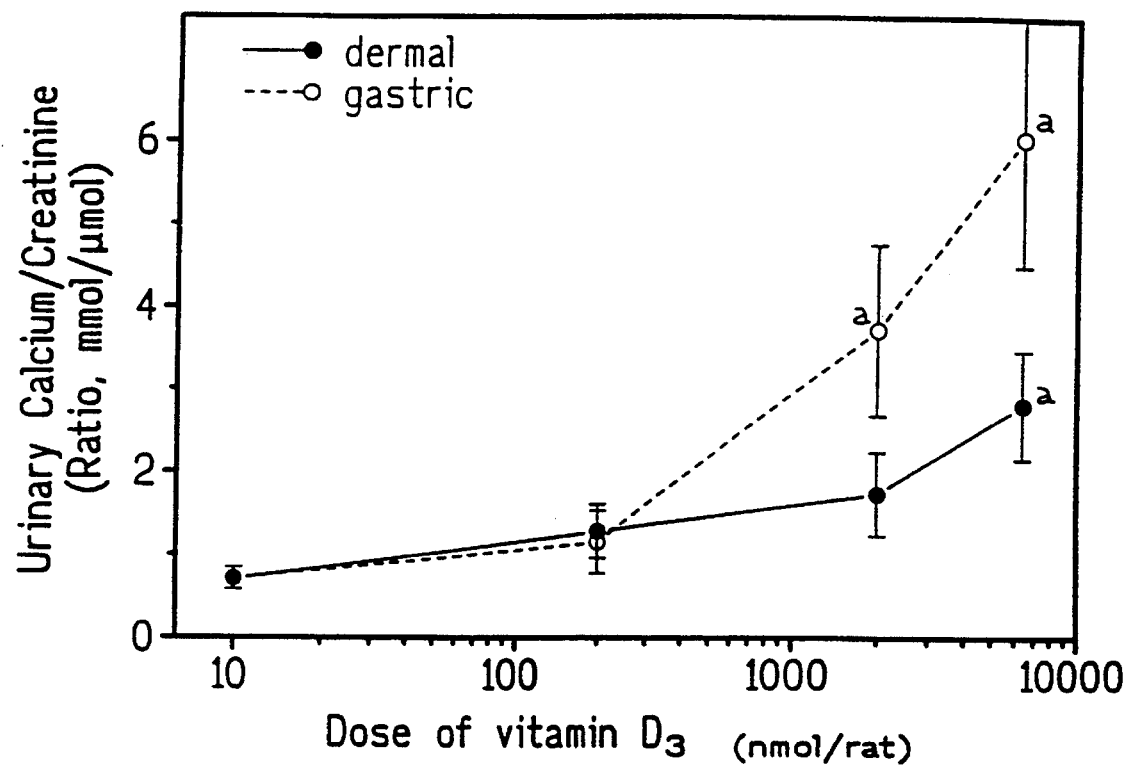
FIG. 6 represents a graph which shows the urinary calcium to creatinine ratio at 48 hours after the gastric or dermal doses of vitamin $D_3$. The graph shows the effect of gastric or dermal vitamin $D_3$ dose on the calcium/creatinine ratio in urine at 38 hours after rats were given a single administration of vitamin $D_3$ by gastric tube or in ethanol onto shaved skin. Each point represents the mean ±SEM of 7 normal, 250-g rats. The points indicated with "a" indicate mean 1,25 (OH)$_2D_3$ values that differed significantly from the losest dose group (ANOVA followed by Dunnet's multiple comparison test).

With gastric treatment, the serum 25(OH)D$_3$ increased in a direct parallel to the dose of vitamin D$_3$ given (FIG. 4). In contrast, with dermal administration, there was a striking plateau in the serum 25(OH)D$_3$ as the dose of vitamin D$_3$ went from 800 μg up to 2600 μg (i.e. 2000–6500 nmol) (FIG. 5). The maximal effect on calcium in the urine was a 6-fold increase with the highest gastric vitamin D$_3$ dose, but by only 2.5-fold increase with the highest dermal treatment (FIG. 6).

It was thus found that during the first two days of treatment, serum 25(OH)D$_3$ does not reach the same levels with dermal vitamin D$_3$ administration as it does with gastric administration. There is evidence of a saturable effect with dermal vitamin D$_3$, whereby a higher dose, in the toxic range, does not result in a further increase in serum 25(OH)D$_3$. The potentially harmful manifestation of an increase in urinary calcium is less with dermal administration.

Experiment 5.

Toxicity: Long-term effects of increasing doses of vitamin D$_3$ given dermally or by gastric tube.

This experiment was to compare potential toxic effects of vitamin D$_3$ given for a 2 wk period, at the near-fatal dose of 800 μg per day by gastric tube, or by dermal administration at 800 μg/day or 2600 μg/day. Another goal was find evidence of saturable dermal uptake by including [$^{14}$C]-vitamin D$_3$ to monitor its removal from the skin at the high doses of vitamin D$_3$.

Method.

Male Wistar rats, 190±10 g were obtained and divided into three groups of 7. They were treated for 2 weeks with one the following: 2000 nmol/day of vitamin D$_3$ by gastric tube; 800 μg/day applied to a 2×2 cm patch of skin on the back; 2600 μg/day skin. The day before killing, 66,000 counts per minute of [$^{14}$C]-vitamin D$_3$ was applied along with the dermal dose to permit a determination of uptake from the skin. The rats were killed after two weeks for analysis of serum, urine, kidney, and aorta. The calcium in urine and acid-treated homogenate of kidney was measured by chemical colorimetry; aorta calcium was measured by treating with nitric acid measuring calcium by atomic absorption.

Results.

These are summarized in TABLE 2. All treatments increased serum calcium above the normal rat value of 2.4 mmol/L, but the gastric treatment had the greatest effect on serum calcium. Likewise, urinary calcium was above the usual rat normal of 1 μmol/mmol creatinine in all these rats. The near-toxic gastric vitamin $D_3$ dose prevented the rats from gaining weight during the 2-wk experiment. With dermal treatment at the same or higher vitamin $D_3$ doses resulted in normal weight gain. The gastric treatment resulted in lower serum 1,25(OH)$_2$D$_3$ concentrations than with either skin group.

Of greatest interest is that the toxic manifestation of calcium accumulation was substantial in both the kidney and the aorta when vitamin $D_3$ was given by gastric tube. However, there was no evidence of either effect in any of the dermally treated rats.

There was no statistical difference in serum 25(OH)D$_3$ between the two dermal groups, despite the three-fold difference in vitamin $D_3$ dose. This lack of a difference also occurred despite the evidence from the [$^{14}$C]-vitamin $D_3$ extracted from the skin of the application site, that the proportion of administered vitamin $D_3$ left in the skin was only marginally affected by the dose.

It was thus most beneficial to note the most ominous signs of vitamin $D_3$ intoxication, namely the calcium deposition in kidney and aorta, and lack of weight gain, were only present with gastric treatment. As in experiment 4, which lasted two days, the present 2-week experiment shows a striking plateau in the serum 25(OH)D$_3$, whereby a more than 3-fold increase in vitamin $D_3$ applied to the skin had no additional effect.

The earlier experiments, 1 to 3, showed that with small, nutritionally relevant amounts of vitamin $D_3$, the dermal route is close to the gastric route in terms of efficiency of delivery and raising 25(OH)D$_3$. However, with the last two experiments, 4 and 5, it is clear that a protective mechanism must be functioning when vitamin $D_3$ enters the body via the skin, to prevent too much of an increase in 25(OH)D$_3$. It is not certain what the mechanism is for this. It is possible that the uptake of vitamin $D_3$ from the skin is saturable by toxic quantities; however, the amount of radiolabel that could be extracted from the treated patch of skin argues against this. Another possibility is that vitamin $D_3$ is handled differently by the body when it enters from the gut, mixed with the chylomicrons like other fats, compared to when it is taken up from the skin, which is the natural mode of entry, and from which vitamin $D_3$ is immediately carried on vitamin $D_3$ binding protein, the specific carrier protein meant for it (Haddad JG, Matsuoka LY, et al, J Clin Invest volume 91:2552; 1993).

TABLE 1 shows biochemical and enzyme data after six weeks of vitamin $D_3$ nutritional supplementation. It shows that gastric and dermal approaches to vitamin $D_3$ nutrition were similarly effective in the longer term;

TABLE 2 shows the results of a toxicity study in which rats were given large doses of vitamin $D_3$ for two weeks either into the stomach, or onto a shaved patch of skin. It shows that with an excessive dose, the gastric administration is far more toxic than is dermal application, and that removal of vitamin $D_3$ from the application site on the skin is only marginally saturable.

TABLE 1

EFFECTS OF DERMAL OR GASTRIC (G1) VITAMIN $D_3$ NUTRITION FOR 6 WEEKS

| Vitamin $D_3$ intake and route | Unit μg/day | 0.08 diet | 0.8 G1 | 8. G1 | 8. dermal |
|---|---|---|---|---|---|
| Serum levels: | | | | | |
| 25(OH)D$_3$ | nmol/day | 3.3 ± 6* | 29 ± 3* | 148 ± 10* | 127 ± 4* |
| Calcium # | nmol/L | 2.38 ± .06 | 2.41 ± .12 | 2.39 ± .12 | 2.58 ± .07 |
| Inorganic phosphate | nmol/L | 2.41 ± .13 | 2.50 ± .15 | 2.19 ± .10 | 2.54 ± .13 |
| Alkaline phosphatase # | U/L | 119 ± 9 | 151 ± 23 | 147 ± 12 | 152 ± 18 |
| Binding Capacity for 25(OH)D$_3$ # | μmol/L | 7.1 ± .3 | 6.93 ± .3 | 7.13 ± .4 | 7.96 ± .2 |
| Renal mitochondria: | | | | | |
| 1α-hydroxylase | fmol/mg/mi | 1052 ± 69 | 993 ± 62 | 539 ± 35 | 630 ± 79 |
| 24-hydroxylase | pmol/mg/mi | 1.34 ± .96 | 3.67 ± 1.2 | 8.88 ± 2.3 | 6.26 ± 1.88 |
| Number of rats per group | | 7 | 7 | 5 | 9 |

\* means are significantly different from each other, p < 0.05
\# Analysis of variance indicated no significant differences for the variable between groups
§ Significantly different from either the 20 nmol/day G1 or skin groups, p < 0.001
■ Significantly different from either the 20 nmol/day g1 or skin groups, p,0.01
¶ Significantly difference from the 20 nmol/day g1 group, <0.05.

TABLE 2

TOXIC EFFECTS AFTER 2 WEEKS OF HIGH DOSES OF DERMAL OR ORAL VITAMIN $D_3$

| Route for Dose | gastric | dermal | dermal |
|---|---|---|---|
| Dose, Vit $D_3$ μg/Day | 800 | 800 | 2600 |
| % [$^{14}$C]-D$_3$ Left on Skin | (not appl) | 47.8% ± 6.1% | 65.6% ± 3.8% |
| Serum 25(OH)D$_3$ | 3553 ± 333 b | 1646 ± 240 | 1409 ± 357 |
| Serum 1,25(OH)$_2$D$_3$ | 258 ± 24 a | 358 ± 23 | 354 ± 33 |

TABLE 2-continued

TOXIC EFFECTS AFTER 2 WEEKS OF HIGH DOSES OF
DERMAL OR ORAL VITAMIN $D_3$

| Route for Dose<br>Dose, Vit $D_3$ µg/Day | gastric<br>800 | dermal<br>800 | dermal<br>2600 |
| --- | --- | --- | --- |
| Weight gain g/2 wk | 7 ± 16 b | 91 ± 7 | 76 ± 8 |
| Serum Calcium nmol/L | 3.89 ± 05 b | 3.43 ± 04 | 3.63 ± 09 a |
| Serum Phosphate nmol/L | 4.53 ± 71 | 3.00 ± 37 | 3.37 ± 68 |
| Urine Ca/create Day 4 | 12.0 ± 1.6 a | 7.9 ± 1.5 | 10.3 ± 6 |
| Urine Ca/create Day 13 | 9.9 ± 1.1 | 10.0 ± .5 | 10.8 ± 1.2 |
| Total Renal Calcium µmol/L | 77 ± 29 b | 13.3 ± .5 | 13.3 ± .5 |
| Total Aorta Calcium nmol | 361 ± 169 b | <10 | <10 |

Values in this Table represent the mean ± SEM of 6 to 8 rats per group.
a, $p < 0.05$ vs dermal 2000 group, two tail t-test, preceded by analysis of variance
b, $p < 0.001$ vs dermal 2000 group Having now generally described this process for providing vitamin D nutrition, it will be apparent to one of ordinary skill in the art that the same can be carried out in a variety of embodiments and variations which may be equivalent without affecting the spirit or scope of the invention or any embodiments of it.

I claim:

1. A method of delivering a nutritional or therapeutic amount of vitamin D to the blood of a mammal, which method comprises topically administering to the skin of the mammal a vitamin D nutritionally or therapeutically-effective amount of a composition comprising a nutritional or therapeutically effective amount of vitamin D in a suitable pharmaceutically-acceptable carrier, diluent or adjuvant therefor.

2. A method as claimed in claim 1 wherein said carrier is an aprotic solvent.

3. A method as claimed in claim 1 wherein said carrier is an alcohol or short chain fatty acid ester.

4. A method as claimed in claim 3 wherein said carrier is ethyl alcohol.

5. A method as claimed in claim 1 wherein said composition comprises 15 to 4000 ug/mL vitamin D.

6. A method as claimed in claim 5 wherein said composition comprises 20–1000 µg/mL vitamin D.

7. A method as claimed in claim 1 further comprising a perfume.

* * * * *